United States Patent [19]
Olofsson et al.

[11] 3,986,511
[45] Oct. 19, 1976

[54] INTRAVAGINAL SANITARY DEVICE
[75] Inventors: Elisabet Olofsson; Bernt Johansson, both of Jarnforsen; Hans-Ivar Eriksson, Ronninge, all of Sweden
[73] Assignee: Mo och Domsjo, Ornskoldsvik, Sweden
[22] Filed: May 9, 1975
[21] Appl. No.: 575,916

[30] Foreign Application Priority Data
May 15, 1974 Sweden .............................. 7406497

[52] U.S. Cl. ................................................ 128/285
[51] Int. Cl.² .......................................... A61F 13/20
[58] Field of Search ........... 128/285, 270, 276, 127, 128/128

[56] References Cited
UNITED STATES PATENTS
1,555,708  9/1925  Gale .................................... 128/285
1,726,339  8/1929  Burill .................................. 128/285
1,977,133  10/1934 Linard ................................ 128/285
2,146,985  2/1939  Rabell ................................ 128/285
2,266,427  12/1941 Levy-Hawes .................... 128/270 X
2,298,424  10/1942 Schreiber .......................... 128/270
2,676,594  4/1954  Milcent ............................. 128/285
3,376,867  4/1968  Kanbar et al. .................. 128/270 X Primary Examiner—Lawrence W. Trapp

[57] ABSTRACT

An absorbent, disposable sanitary device for insertion in a body cavity, and especially intended for insertion into the vagina to absorb menstrual fluid therein, comprising a resilient rotund absorbent fibrous layer which retains its resiliency when wet and in which fibers are bonded together, supported on a core of stiff material, and means attached to the core to facilitate removal of the device from the vagina or other body cavity.

18 Claims, 4 Drawing Figures

INTRAVAGINAL SANITARY DEVICE

There are a number of sanitary devices known to the art which are intended to be inserted into a body cavity, such as into the vagina, for the purpose of collecting and/or absorbing menstrual fluid therein. The most commonly used intravaginal sanitary device is the sanitary tampon, a hard, compacted fibrous mat formed into a cylinder.

Such tampons characteristically are compressed to a hard, substantially cylindrical body about 12 to 16 mm in diameter and about 40 to 60 mm long. The compression makes them extremely rigid, and because of this and their relatively small cross-sectional area they are readily insertable into and removable from the vagina. Sanitary tampons do however have a number of serious disadvantages.

For example, because of the relatively small cross-sectional area the tampons do not fit snugly into the vagina, in a leak-tight seal with the walls thereof about their entire circumference, and in consequence may permit menstrual fluid to seep out between the walls of the vagina and the outer surface of the tampon. Furthermore, the stiffness of the tampons together with their relatively long length makes it relatively easy to insert them too far into the vagina, so that the tampons may be positioned obliquely therein so as to lie partially to one side of the cervic (the neck of the uterus), which further accentuates the risk of leakage. Also, because the tampons are relatively long, slender and rigid, an uncomfortable pressure is liable to be exerted by the tampons onto the cervix and portio (the mouth of the uterus). Their stiffness and length make them susceptible to shift in position with movement of the body, which further increases the risk of leakage, and may also cause discomfort, as a result of pressure against the cervix and portio.

The compacted fibrous material of the tampon has a low rate of swelling when wet with menstrual liquid, and will only expand to a small extent, which limits their potential absorbency for liquid. Because of the limited expansion the tampons will not swell sufficiently to fill the cross-sectional area of the vagina; even a wet tampon may leak.

Another type of intravaginal sanitary device is made of a porous foam or cellular plastic material, such as polyurethane, for example. Different embodiments of plastic foam, sponges, and like cellular products are described in the literature. Such products, for example, may be formed of a single piece of plastic foam or sponge or cellular material, or of several pieces of plastic foam or cellular material, enclosed in a liquid-permeable casing. These tampons also have serious disadvantages, of which one is that they cannot normally be introduced into the vagina without the use of a separate inserting device.

A third category of intravaginal sanitary device is nonabsorbent, and relies on a plug or stopper effect. Such products are made of a soft plastic material having an appropriate shape so that when placed in the lower region of the vagina at the entrance thereto, they are retained in position by the levator muscles. These products may be in the form of a receptacle to collect fluid and/or exert a damming effect. When removed from the vagina, these products must be emptied of menstrual liquid and washed so that they can be reused. Many users consider this procedure troublesome and distasteful.

The present invention provides a sanitary device for insertion into a body cavity that overcomes substantially all of the aforementioned disadvantages. The intravaginal sanitary device of the invention comprises a resilient rotund absorbent fibrous layer which retains its resiliency when wet, supported on a core of stiff material, and means attached to the core for the removal of the device from the body cavity. The absorbent layer comprises a reticulated structure composed of fibers bonded together in a cohesive porous layer.

Figure 1:
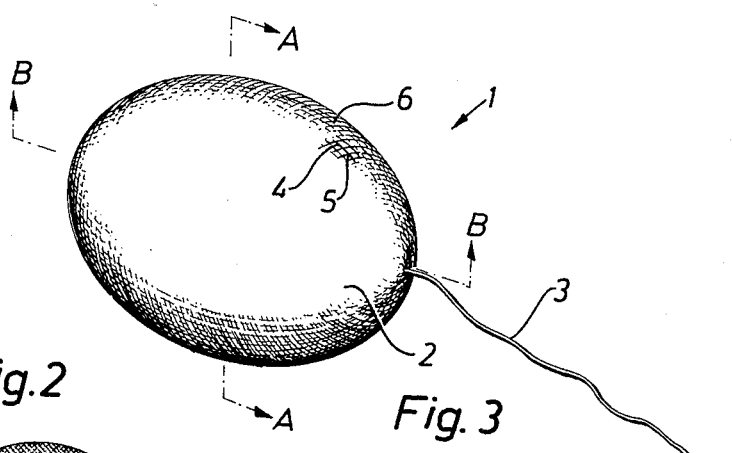
FIG. 1 is a perspective view of a sanitary device in accordance with the invention.

As seen in FIGS. 1 to 4, the sanitary device 1 of the illustrated embodiment comprises a rotund absorbent layer 2 of fibrous material 4, supported on a rigid core 7. A cord 3 is attached to the core 7 (see FIG. 3), and makes it possible to draw the device from the vagina. The absorbent layer 2 comprises an intermingled and interlocked mat of fibers 4, which contact each other at their crossing points in a large number of positions 5. At certain of these positions 5, the fibers are bonded together to form a reticulated fibrous structure 6. Since it is not possible to show each crossing point 5, owing to the large number thereof, the fibers 4 and the positions 5 are only symbolically shown in FIG. 1. Because the fibers 4 are bonded together at positions 5, the absorbent layer 2 is both resilient and strong, and retains its resiliency when wet. The fibers 4 at the same time are held apart in spaced positions in the reticulated structure, which in consequence has a plurality of interconnecting interstices between the fibers, and is therefore quite porous and absorbent. The number of fibers per unit volume, i.e., the density of the layer, is selected so that the open volume as interstices therebetween is quite high, resulting in extremely good absorbent properties. The excellent absorbent properties are demonstrated in Examples 1 and 2. The density of the absorbent layer and the types of fibers composing it also significantly contribute to its mechanical strength, its resiliency and its ability to retain its resiliency when wet. A nice balance in these properties is obtained when the density is within the range from about 0.05 to about 0.15 g/cm$^3$.

Any known method of bonding fibers together can be used to form a reticulated structure 6 in the absorbent layer of the invention. The bonds between the fibers 4 can be obtained by applying thereto a thermoplastic, i.e., heat-softenable, bonding agent in solution, emulsion, or powdered form. Any known thermoplastic resin can be used, such as a polyacrylate, polyamide, polyester, polyvinylidene chloride, polyacrylonitrile, polyvinyl acetate, polystyrene-butadiene, or polyvinyl chloride resin, and then heat-softening the bonding agent so as to adhere to and bond the fibers at their crossing points. Bonding agents which do not require heat in order to create a bond between the fibers can also be used.

Another method of bonding the fibers involves the introduction of a thermoplastic netting of extruded or woven or cross-laid filamentary material into the layer 2. The thermoplastic fibrous material of such a net may comprise for example, polyethylene, polypropylene, polyamide, polyester, poly (ethylene-vinyl acetate), and poly (vinyl chloride-vinyl acetate) fibers. Heating of the layer 2 is also required in this case, in order to soften the plastic and create bonds between the fibers.

In a preferred embodiment of the invention, the absorbent layer comprises a mixture of thermoplastic and nonthermoplastic fibers, which are bonded together by blowing warm air through the fibrous mass. In this way, the thermoplastic fibers are softened and made tacky, and bond to one another and to the nonthermoplastic fibers. If the temperature of the air is sufficiently high, the thermoplastic fibers can be completely melted. The absorbent layer, however, may also comprise only thermoplastic fibers or only absorbent fibers. Thermoplastic fibers are substantially nonabsorbent, and the absorbent properties of the layer are somewhat lower than if only absorbent natural or synthetic fibers are used, or than if a mixture of absorbent natural and/or synthetic fibers and thermoplastic fibers is used. Examples of suitable thermoplastic fibers include polyethylene, polypropylene, polyacrylonitrile, polyvinyl chloride, polyamide and polyester fibers. The absorbent natural and synthetic fibers include cellulose fibers such as cotton, linen, ramie, jute, sisal, hemp, wool, mohair, and viscose rayon. Among the thermoplastic nonabsorbent fibers preferred are those of the polyolefin type, such polyethylene and polypropylene, while among the absorbent fibers, viscose rayon fibers are preferred.

In mixtures, any relative proportions can be used, ranging from 1 to 99% of one, and 99% to 1% of the other. In the case of polypropylene and rayon, from 15 to 75% polypropylene and from 85 to 25% rayon is suitable. The length of the fibers is not critical, but should suitably exceed 15 mm. Lengths in excess of 300 mm are impractical, and lengths below 150 mm are preferred. It is also preferred that the different fibers all be of the same length, but there can be variations in lengths between, for example, two types of fibers. The fibers are usually first mixed and then carded to a carded web in the form of a band or strip.

The titre of the fiber greatly affects the resiliency of the absorbent layer, and its ability to retain its resiliency when wet. The titre is preferably selected within the range from about 1.5 to about 15 decitex, or from about 1.4 to about 13.5 denier (decitex = weight in grams of a fiber 10,000 meters long; denier = the weight in grams of a fiber 9000 meters long).

The shape of the absorbent layer 2 is of course the external shape of the device, and is extremely important for satisfactory functioning of the sanitary device 1. The device and layer should be rotund, i.e., rounded on all sides, and generally greater in girth at a central portion than at its ends. An ellipsoidal shape is preferred, but a spherical shape is also satisfactory.

Nonuniform ellipsoids and spheres are more usual, because of the difficulty in precisely shaping the external configuration of a fibrous mass. In the case of the ellipsoid or other elongated rotund or egg-shaped structure, the ratio between the length of the minor axis to the length of the major axis should be within the range from about 1 to about 0.4, preferably from about 0.9 to about 0.6. If the ratio is below 0.4, there is a risk that menstrual liquid will seep past the sanitary device. A suitable length of the minor axis is within the range from about 25 to about 45 mm, and of the major axis is within the range from about 25 to about 55 mm.

A protective sheath of liquid-permeable material may be arranged around the exterior of the absorbent layer 2.

Figures 2, 3:
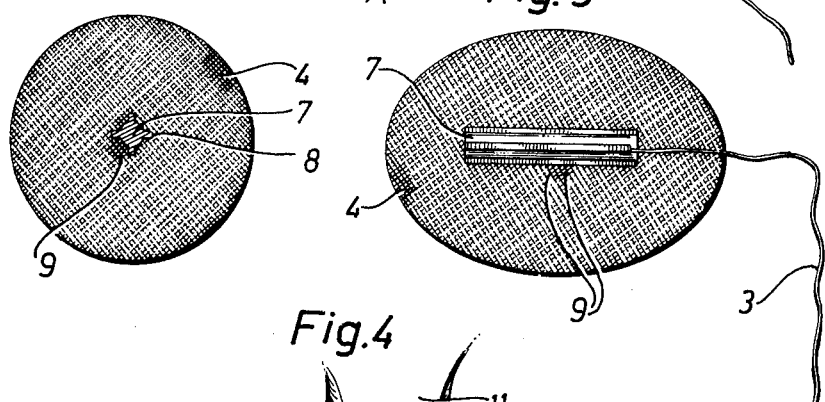
FIG. 2 is a cross-sectional view taken along the line A-A of the device of FIG. 1.
FIG. 3 is a cross-sectional view taken along the line B-B of the device of FIG. 1.

As will be seen from FIG. 2, a supporting core 7 is disposed in the center of the absorbent layer 2. The core 7 is surrounded by a sufficient thickness of layer 2 that it does not cause discomfort to the wearer of the sanitary device 1 at any time. The core is elongated, and may have any shape whatsoever in cross section. For example, the length of the core can be from about 50 to about 90% of the length of the absorbent layer and the width can be from about 10% to about 30% of the width of the absorbent layer 2. The core can be solid, cellular or hollow, and the external surface thereof can be smooth, or can be provided with depressions such as grooves and/or projections such as ribs, for example in the form of longitudinally extending ribs 8, such as those shown in FIG. 2.

The core can be made from any rigid material that is preferably inexpensive, for example, plastic materials such as polyethylene, polypropylene, polystyrene, polyvinyl chloride and polyamide. Another suitable core material is cardboard. The core may also comprise bonded thermoplastic fibers, similar to those incorporated in the absorbent layer 2. The core may be absorbent or nonabsorbent, but any liquid which is absorbed must not disadvantageously affect the rigidity of the core.

The core 7 can be firmly bonded to the absorbent layer 2 (for example by means of an adhesive) or securely attached thereby by interlocking the fibers 9 located nearest the core 7 with the projections or depressions on the surface of the core.

The means for withdrawing the device 1 is a cord 3 securely attached to the core 7. Any filamentary material can be used, such as string or braided or woven yarn. The means or cord 3 preferably is made of a material which does not wick, i.e. a material such as that normally used for the withdrawal cords of sanitary tampons.

The main function of the core is to permit the user to insert the sanitary device in the body cavity in a most acceptable manner. The attachment of the means for withdrawal such as a cord to the core greatly faciliates the removal of the sanitary device from the body cavity.

The sanitary device according to the present invention can be introduced into the body cavity such as a vagina without the aid of separate means, for example, so-called insertion sleeves. However, of course the sanitary device of the invention can also be inserted with the aid of an insertion sleeve, if desired.

Figure 4:
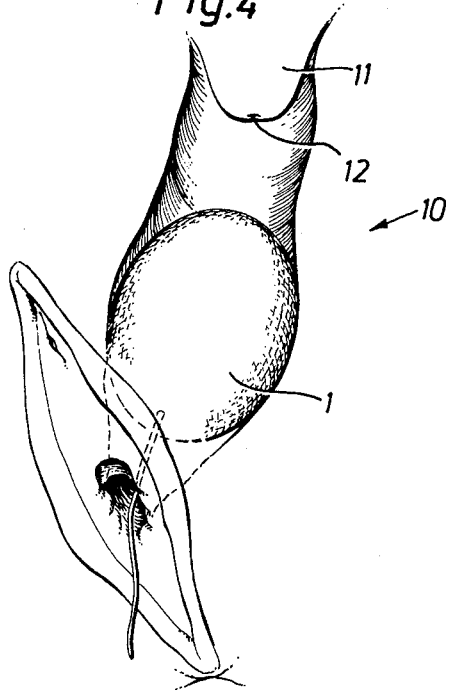
FIG. 4 shows diagrammatically the device of FIGS. 1 to 3 inserted in a vagina.

The sanitary device of the invention has practically no tendency to permit leakage of menstrual liquid, and its ability to absorb menstrual liquid is extremely high. FIG. 4 shows the sanitary device 1 of the invention inserted in a vagina 10. As previously mentioned, leakage of menstrual fluid past a cylindrical tampon can arise if the tampon, after insertion into the vagina or during use moves into an askew position in the vagina, i.e. a large portion of the tampon becomes located on one side of the cervix 11, and therewith also to one side of the portio 12, through which the menstrual fluid flows. A cylindrical tampon may go askew upon violent or accentuated movement by the wearer, for example as a result of lifting heavy objects. It has also been established that when a woman stands upright, the cervix moves further down the vagina 10 and shortens the same, which may shift a cylindrical tampon. Furthermore, as mentioned previously, cylindrical tampons are also liable to exert pressure on the cervix, thereby causing discomfort.

After insertion, a sanitary device in accordance with the invention remains in the correct position, in the lower portion of the vagina 10, as shown in FIG. 4, during the period of its insertion, and there is no risk that the device will reach a position in the vagina 10 where menstrual fluid is liable to leak past the device, or where the wearer will suffer discomfort as a result of the device. The sanitary device 1 according to the invention is able to prevent leakage of menstrual fluid past the same and to absorb such menstrual fluid, because of its rotund, for example, ellipsoidal, shape, its size, its softness, and its resiliency. These properties enable the device to conform to the irregular cross-sectional shape of the vagina 10. A sanitary device constructed in accordance with the invention remains reliably in position, even though the wearer moves about violently or energetically. Owing to the high degree of resiliency possessed by the device when wet, the device will not change its position in the vagina subsequent to the initial absorption of menstrual fluid, but is retained in position while it is in use.

The sanitary device according to the invention has been successfully tested in practice, and the results are given in the following Examples.

EXAMPLE 1

The sanitary device according to the invention was compared with three different types of cylindrical tampons.

The sanitary device according to the invention comprised a core in the form of a polyethylene tube to which a layer of intermingled fibers was applied, so as to obtain a substantially ellipsoidal shape. The polyethylene tube had a length 35 mm, a diameter of 7 mm, and a wall thickness of 0.5 mm. The fibers comprised a mixture of 50% viscose rayon fibers, having a length of 40 mm and a titre or fineness of 1.7 decitex = 1.5 denier, and 50% polypropylene fibers having a length of 40 mm and a titre of 3.5 decitex = 3.2 denier. The fibers located adjacent the polyethylene tube were bonded to the tube with an adhesive, and the remaining fibers were heat-bonded together by blowing warm air thereonto, and then cooling. The device overall had a length of the minor axis of 35 mm, and the length of the major axis was 45 mm. The ratio of the minor axis to the major axis was 0.78. The withdrawal cord was a section of hydrophobic non-wicking cotton yarn, which was firmly attached to the polyethylene tube. The weight of the device was 3.9 g (3.4 g absorbent layer, 0.35 g core, and 0.15 g withdrawal cord) and its volume was 30 cm³. The density of the device was 0.011 g/cm³.

The conventional tampons were of cylindrical configuration, and their dimensions are shown in Table I below.

TABLE I

| | | Cylindrical Tampon | | |
|---|---|---|---|---|
| | | I | II | III |
| Weight | g | 4.0 | 4.0 | 3.6 |
| Length | mm | 55 | 45 | 50 |
| Diameter | mm | 13 | 16 | 14 |
| Volume | cm³ | 7.5 | 9 | 7.7 |
| Density | g/cm³ | 0.53 | 0.44 | 0.47 |
| Fiber | | 100% rayon | 100% rayon | 75% rayon 25% cotton |

The tests were carried out on three women, who used the conventional tampons, I, II and III and also the sanitary device according to the invention as part of a normal routine. The results are shown in Table II.

TABLE II

| | | Absorbency | | | |
|---|---|---|---|---|---|
| Device | Device average weight g | Quantity of menstrual fluid absorbed g fluid/ g device | Quantity of menstrual fluid absorbed per device g fluid | Period of use hours | Number of devices used |
| Cylindrical Tampon I | 4.0 | 1.3 | 5.2 | 2 18/60 | 32 |
| Cylindrical Tampon II | 4.0 | 1.2 | 4.8 | 2 49/60 | 30 |
| Cylindrical Tampon III | 3.6 | 2.0 | 7.2 | 2 21/60 | 28 |
| Sanitary device according to the invention | 3.9 | 3.4 | 13.3 | 4 17/60 | 26 |

The parameter "period of use" recited in Table II corresponds to the period of time for which the wearers considered the device safe to use. The wearers replaced the devices when they were considered saturated, i.e. no longer able to absorb more menstrual fluid, at which time there was a risk that menstrual fluid would leak past the products.

As seen in Table II, the sanitary device according to the invention has a greater absorbency per gram, and a greater total absorbency, and can be used for a much longer time than the conventional tampons, i.e. considerably fewer changes of the device are needed, during a menstruation period. Consequently, the absorbency of the sanitary device according to the invention is much higher than the absorbency of the conventional tampons, even when the different periods of use are taken into account.

The above mentioned tests were made on women having a normal flow of menstrual fluid. The effect afforded by a sanitary device according to the invention with women who experience a copious flow of menstrual fluid is shown in the Table III below.

EXAMPLE 2

The devices tested in this Example were the same as the devices tested in conjunction with Example 1. Their average weights were different, due to the fact that the number of devices tested in this Example differed from the number of devices tested in Example 1.

TABLE III

| Device | Device average weight g | Absorbency Quantity of menstrual fluid absorbed per g g fluid/ g device | Quantity of menstrual fluid per device g fluid | Period of use hours | Number of devices used |
|---|---|---|---|---|---|
| Cylindrical Tampon I | 4.2 | 1.8 | 7.6 | 1 | 3 |
| Cylindrical Tampon II | 4.0 | 1.6 | 6.3 | 1 15/60 | 4 |
| Cylindrical Tampon III | 3.6 | 1.8 | 6.1 | 1 10/60 | 4 |
| Sanitary device according to the invention | 4.1 | 4.7 | 19.2 | 2 | 3 |

As seen from Table III, the period of use in this Example is shorter than that shown in Example 2. The sanitary device according to the invention can also be worn for a much longer period of time in this case than can the conventional tampons. The difference in absorbency of the sanitary device according to the invention as compared with the conventional tampons is more pronounced when the wearer has a copious flow of menstrual fluid, as can be seen by comparing Tables II and III.

Having regard to the foregoing disclosure, the following is claimed as the inventive and patentable embodiments thereof:

1. A sanitary device for insertion into a body cavity comprising a resilient rotund absorbent fibrous layer having a reticulated cohesive porous structure in which fibers are bonded together in a manner to define interstices therebetween, and which retains its resiliency when wet; a core of stiff material embedded in and supporting the fibrous layer; and means attached to the core for the removal of the device from the body cavity.

2. A sanitary device according to claim 1 in which the absorbent layer comprises an intermingled and interlocked mat of fibers which are bonded together to form the reticulated fibrous structure.

3. A sanitary device according to claim 1 in which the absorbent layer has a substantially ellipsoidal configuration.

4. A sanitary device according to claim 3 in which the ratio of the length of the minor axis to the length of the major axis of the ellipsoidal absorbent layer lies within the range from about 1 to about 0.4.

5. A sanitary device according to claim 1 in which the absorbent layer has a substantially spheroidal configuration.

6. A sanitary device according to claim 1 in which fibers of the absorbent layer are attached to the core.

7. A sanitary device according to claim 1 in which the fibers are of thermoplastic material and are self-bonded together.

8. A sanitary device according to claim 7 in which the fibers comprise a mixture of thermoplastic and absorbent fibers.

9. A sanitary device according to claim 1 in which the absorbent layer is enclosed in a liquid-permeable sheath.

10. A sanitary device according to claim 1 in which the rigid core comprises self-bonded thermoplastic fibers.

11. A sanitary device according to claim 1 in which the density of the absorbent layer is within the range from about 0.05 to about 0.15 g/cm$^3$.

12. A sanitary device according to claim 1 in which the fibers are bonded together with a bonding agent.

13. A sanitary device according to claim 1 in which the means attached to the core for the removal of the device from the body cavity is of filamentary material.

14. A sanitary device according to claim 13 in which the filamentary material is non-wicking.

15. A sanitary device according to claim 1 in which the core is elongated.

16. A sanitary device according to claim 15 in which the core is tubular.

17. A sanitary device according to claim 1 in which the core has a ribbed surface.

18. A sanitary device according to claim 1 in which the fibers comprise a mixture of polypropylene and regenerated cellulose fibers, and the core is a polyethylene tube.

* * * * *